United States Patent
Schwemberger et al.

(10) Patent No.: US 8,821,520 B2
(45) Date of Patent: Sep. 2, 2014

(54) LOADER FOR KNOTTING ELEMENT

(75) Inventors: Richard F. Schwemberger, Cincinnati, OH (US); John L. Stammen, Cincinnati, OH (US); Michael S. Cropper, Edgewood, KY (US); Jonathan A. Coe, Cincinnati, OH (US); James W. Miser, Jr., Batavia, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1760 days.

(21) Appl. No.: 11/744,271

(22) Filed: May 4, 2007

(65) Prior Publication Data

US 2008/0275475 A1 Nov. 6, 2008

(51) Int. Cl.
*A61B 17/04* (2006.01)
*A61B 19/00* (2006.01)
*A61B 17/00* (2006.01)

(52) U.S. Cl.
CPC ....... *A61B 17/0487* (2013.01); *A61B 2019/307* (2013.01); *A61B 17/0469* (2013.01); *A61B 2017/0053* (2013.01); *A61B 2017/0488* (2013.01); *A61B 2017/0479* (2013.01); *A61B 17/0485* (2013.01)
USPC ............................. 606/148; 606/139; 606/144

(58) Field of Classification Search
USPC .................. 606/144, 148, 145–147
See application file for complete search history.

(56) References Cited

U.S. PATENT DOCUMENTS

| | | |
|---|---|---|
| 4,235,238 A | 11/1980 | Ogiu et al. |
| 4,669,473 A | 6/1987 | Richards et al. |
| 4,741,330 A | 5/1988 | Hayhurst |
| 5,002,550 A | 3/1991 | Li |
| 5,041,129 A | 8/1991 | Hayhurst et al. |
| 5,046,513 A | 9/1991 | Gatturna et al. |
| 5,269,809 A | 12/1993 | Hayhurst et al. |
| 5,307,924 A | 5/1994 | Manosalva et al. |
| 5,336,229 A * | 8/1994 | Noda .............................. 606/144 |
| 5,341,823 A | 8/1994 | Manosalva et al. |
| 5,464,425 A | 11/1995 | Skiba |
| 5,470,337 A | 11/1995 | Moss |
| 5,531,763 A | 7/1996 | Mastri et al. |
| 5,591,181 A * | 1/1997 | Stone et al. .................... 606/144 |
| 5,591,202 A | 1/1997 | Slater et al. |
| 5,626,614 A | 5/1997 | Hart |

(Continued)

FOREIGN PATENT DOCUMENTS

| | | |
|---|---|---|
| EP | 746239 B1 | 9/2002 |
| EP | 1447052 A2 | 8/2004 |

(Continued)

OTHER PUBLICATIONS

International Search Report dated Nov. 11, 2008 for corresponding patent application PCT/US/2008/062203.

*Primary Examiner* — Corrine M McDermott
*Assistant Examiner* — Alexander Orkin

(57) ABSTRACT

A device for loading a surgical knotting element on an applicator tool. One embodiment of the device includes a channel dimensioned to receive an applicator tool comprising a coupling. A surgical knotting element comprises a coupling complementary to the coupling of an applicator tool and a suture path. A carriage receives the surgical knotting element. The carriage is moveable in a transverse direction relative the channel between a first position where the knotting element is misaligned with the channel and a second position where the couplings are engaged with one another.

8 Claims, 6 Drawing Sheets

(56) References Cited

U.S. PATENT DOCUMENTS

| | | | |
|---|---|---|---|
| 5,630,824 A | 5/1997 | Hart | |
| 5,715,942 A * | 2/1998 | Li et al. | 206/339 |
| 5,741,300 A * | 4/1998 | Li | 606/232 |
| 5,755,730 A | 5/1998 | Swain et al. | |
| 5,800,445 A | 9/1998 | Ratcliff et al. | |
| 5,814,069 A * | 9/1998 | Schulze et al. | 606/228 |
| 5,846,254 A * | 12/1998 | Schulze et al. | 606/148 |
| 5,899,921 A | 5/1999 | Caspari et al. | |
| 5,902,321 A | 5/1999 | Caspari et al. | |
| 5,954,747 A | 9/1999 | Clark | |
| 6,068,648 A | 5/2000 | Cole et al. | |
| 6,086,608 A | 7/2000 | Ek et al. | |
| 6,200,329 B1 | 3/2001 | Fung et al. | |
| 6,231,592 B1 | 5/2001 | Bonutti et al. | |
| 6,368,334 B1 | 4/2002 | Sauer | |
| 6,500,184 B1 | 12/2002 | Chan et al. | |
| 6,524,328 B2 | 2/2003 | Levinson | |
| 6,533,796 B1 * | 3/2003 | Sauer et al. | 606/144 |
| 6,566,484 B2 | 5/2003 | Gharda et al. | |
| 6,663,639 B1 | 12/2003 | Laufer et al. | |
| 6,699,263 B2 | 3/2004 | Cope | |
| 6,881,816 B2 | 4/2005 | Gharda et al. | |
| 6,909,015 B2 | 6/2005 | Kemmish et al. | |
| 7,048,755 B2 | 5/2006 | Bonutti et al. | |
| 7,112,207 B2 | 9/2006 | Allen et al. | |
| 7,427,279 B2 | 9/2008 | Frazier et al. | |
| 2003/0040760 A1 | 2/2003 | Hnojewyj et al. | |
| 2003/0158581 A1 | 8/2003 | Levinson | |
| 2003/0163160 A1 | 8/2003 | O'Malley et al. | |
| 2003/0171760 A1 | 9/2003 | Gambale | |
| 2003/0191497 A1 | 10/2003 | Cope | |
| 2003/0208209 A1 * | 11/2003 | Gambale et al. | 606/144 |
| 2004/0093023 A1 | 5/2004 | Allen et al. | |
| 2004/0122473 A1 | 6/2004 | Ewers et al. | |
| 2004/0133238 A1 | 7/2004 | Cerier | |
| 2004/0153103 A1 | 8/2004 | Schwartz et al. | |
| 2004/0186514 A1 | 9/2004 | Swain et al. | |
| 2004/0260344 A1 | 12/2004 | Lyons et al. | |
| 2005/0234512 A1 | 10/2005 | Nakao | |
| 2005/0251157 A1 | 11/2005 | Saadat et al. | |
| 2005/0251202 A1 | 11/2005 | Ewers et al. | |
| 2006/0009789 A1 | 1/2006 | Gambale et al. | |
| 2006/0015125 A1 | 1/2006 | Swain | |
| 2006/0079914 A1 | 4/2006 | Modesitt et al. | |
| 2006/0106405 A1 | 5/2006 | Fann et al. | |
| 2007/0060929 A1 * | 3/2007 | Onishi et al. | 606/139 |
| 2007/0112359 A1 * | 5/2007 | Kimura et al. | 606/142 |
| 2007/0162052 A1 * | 7/2007 | Hashimoto et al. | 606/139 |
| 2007/0270908 A1 | 11/2007 | Stokes et al. | |

FOREIGN PATENT DOCUMENTS

| | | |
|---|---|---|
| EP | 1632186 A2 | 3/2006 |
| JP | 2004/358045 A | 12/2004 |
| WO | WO 94/22381 A1 | 10/1994 |
| WO | WO 01/89393 A1 | 5/2001 |
| WO | WO 01/66001 A2 | 9/2001 |
| WO | WO 02/094108 A2 | 11/2002 |
| WO | WO 03/034895 A | 5/2003 |
| WO | WO 2006/044837 A2 | 4/2006 |

* cited by examiner

LOADER FOR KNOTTING ELEMENT

BACKGROUND

The following disclosure relates to surgery, with one embodiment relating to endoscopic surgical techniques and devices. Surgery generally refers to the diagnosis or treatment of injury, deformity, or disease. A wide variety of surgical techniques have been developed. One type of surgery is called minimally invasive surgery, which typically involves entering the body through the skin or through a body cavity or anatomical opening while minimizing damage to these structures. Minimally invasive medical procedures usually involve less operative trauma for the patient compared to open surgical procedures. Minimally invasive surgical procedures are also generally less expensive, reduces hospitalization time, causes less pain and scarring, and reduces the incidence of complications related to the surgical trauma, thus speeding the recovery.

Endoscopes are often used during minimally invasive surgical procedure to visualize the organs and structures inside the body. Endoscopes generally use a light delivery system to illuminate the tissue under inspection. Typically the light source is outside the body and the light is typically directed via an optical fiber system. Images are captured, usually through a lens system, and transmitting to a monitor. Some endoscopes include working channels through which medical instruments may be introduced into the body to biopsy or operate. Working channels can also be independent of the endoscope. Endoscopes may be rigid or flexible. Some flexible endoscopes are steerable to facilitate positioning the endoscope in the body.

Sutures are often used during surgical procedures to hold skin, internal organs, blood vessels, and other tissues in the body. A suture is typically an elongate flexible filament, but may take a variety as different thread or thread-like structures, including without limitation fibers, lines, wires, and the like. A suture may be a homogeneous or heterogeneous, and may also comprise a single filament or a composite suture, such as a two or more twisted or woven filaments. In addition, a suture may be made from a wide array of absorbable (i.e., metabolized by the body) or non-absorbable materials known in the art.

A variety of different techniques and devices have been developed to deliver and attached sutures to tissue. Some techniques involve piercing tissue with needles, tying or forming knots or loops, delivering anchors such as t-tags, x-tags and other flexible or rigid anchors, and the like. Other suturing techniques involve creating loops around anatomy. Sutures often need to be fastened. Time and space constraints, often present in minimally invasive surgical procedures, makes traditional tying of knots impractical, so mechanical knotting elements are often used. Disclosed herein are novel devices and methods relating to threading, loading, and deploying knotting elements.

BRIEF DESCRIPTION OF DRAWINGS

While the specification concludes with claims that particularly point out and distinctly claim the invention, it is believed the invention will be better understood from the following description taken in conjunction with the accompanying drawings illustrating some non-limiting examples of the invention. Unless otherwise indicated, like reference numerals identify the same elements.

DETAILED DESCRIPTION

FIGS. 1-4 depicts an embodiment of a loader (10). The loader (10) is used facilitate loading the knotting element (40) onto an applicator (30). The applicator (30) is used to deliver the knotting element (40) into the desired location during surgery. In the present embodiment, the applicator (30) is a flexible endoscopic tool designed for use in a working channel of a flexible endoscope, but other types of surgical applicators are also contemplated such as rigid or articulated applicators.

Figure 1:
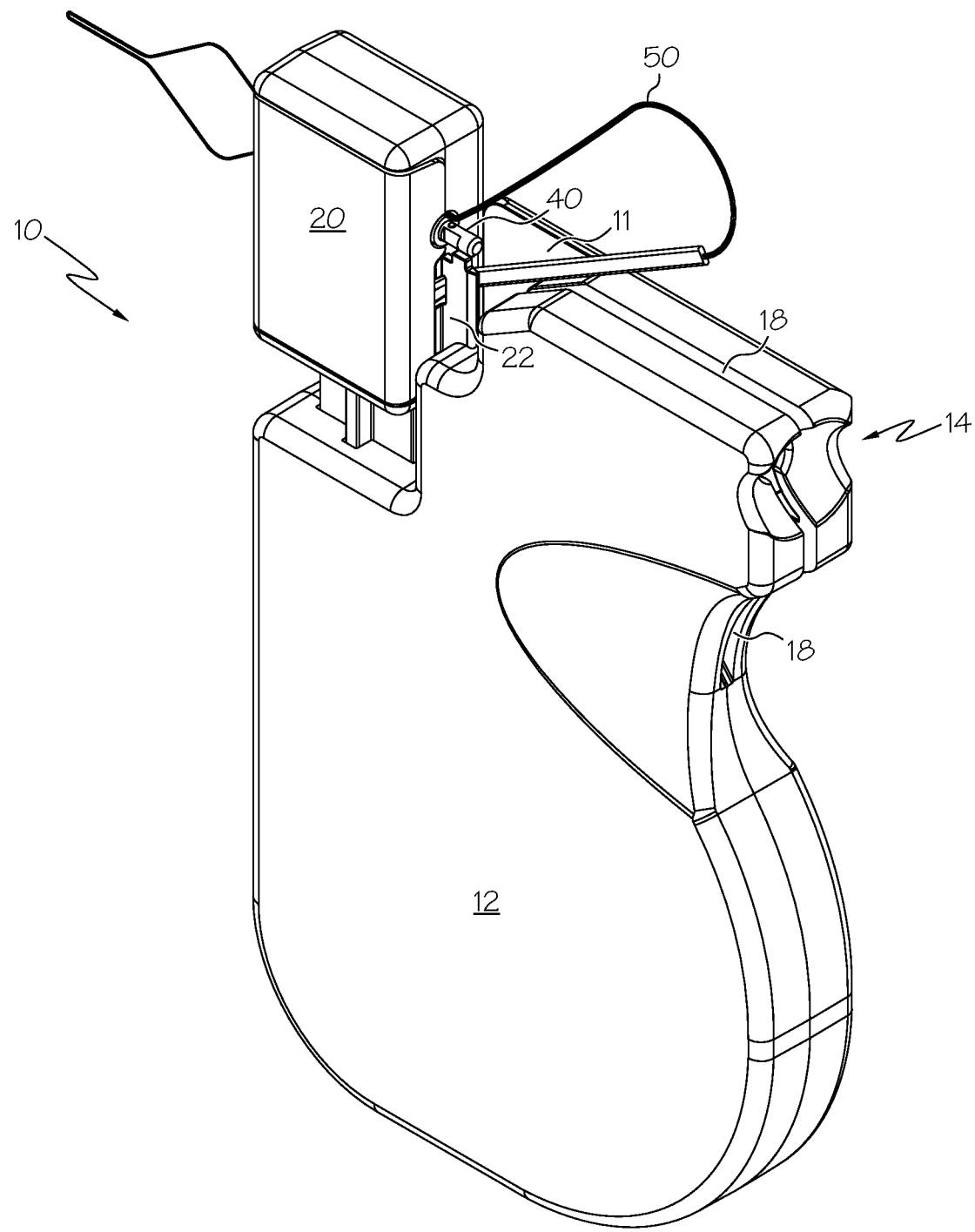
FIG. 1 depicts an isometric view of a knotting element loader.
Figure 2:
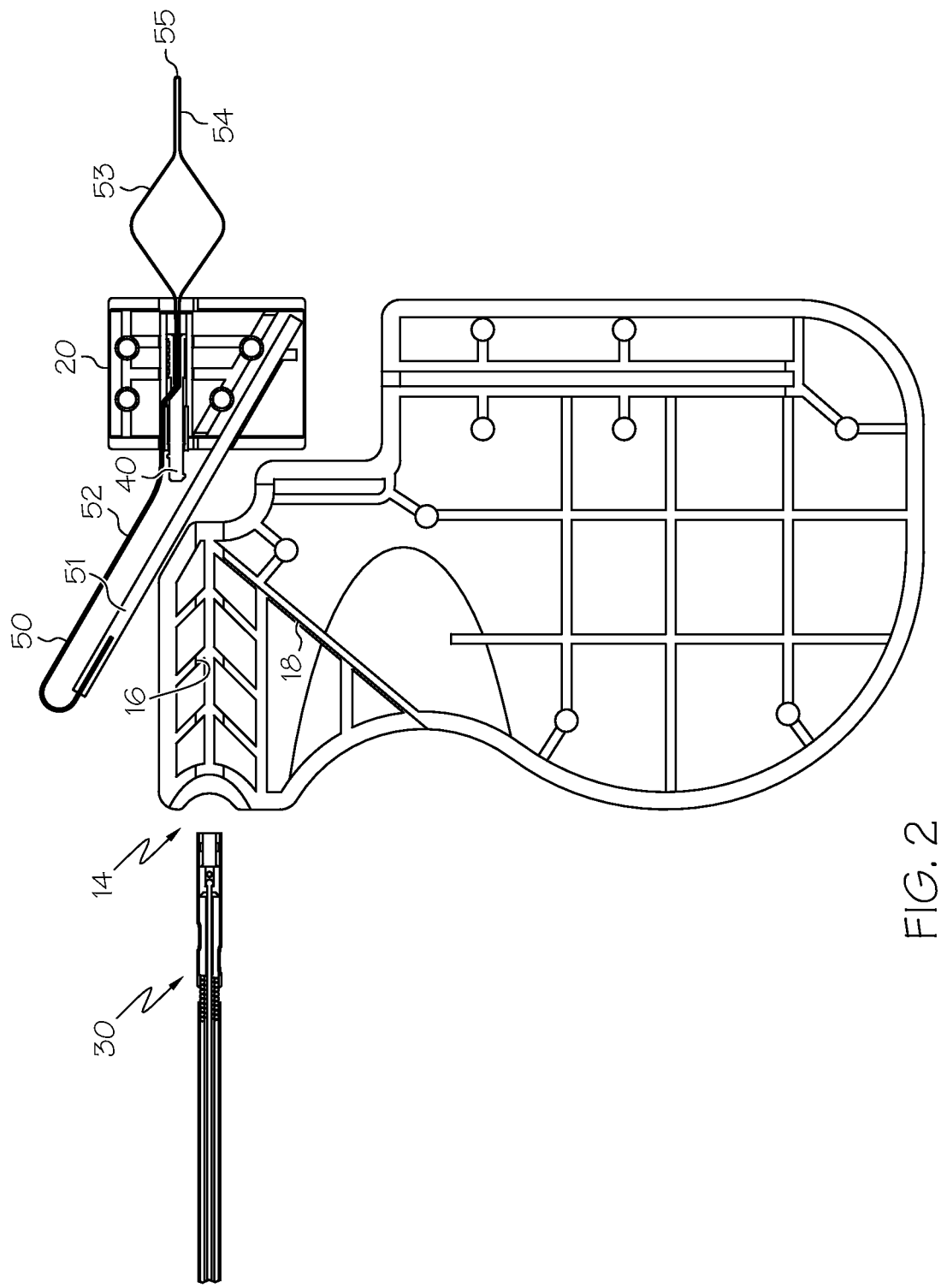
FIG. 2 depicts a side view of a knotting element loader with half the housing removed to illustrate internal components.

The loader (10) includes a housing (12), a carriage (20), and a threader (50). The carriage (20) moves vertically relative the housing (12). Preferably, the carriage (20) will be preloaded with a knotting element (40) and the threader (50) will be preloaded in the knotting element (40), as shown in FIGS. 1-2. The carriage (20) includes a length of silicone tubing that provides a resilient interference fit to frictionally hold the knotting element (40) in the carriage (20). The housing (12) includes a port (14) that opens to a horizontal channel (16) dimensioned to receive the applicator (30). A transverse slot (18) bisects the channel (16). Optionally, the housing (12) may be transparent to visualize objects in the channel (16) and slot (18).

Figure 5:
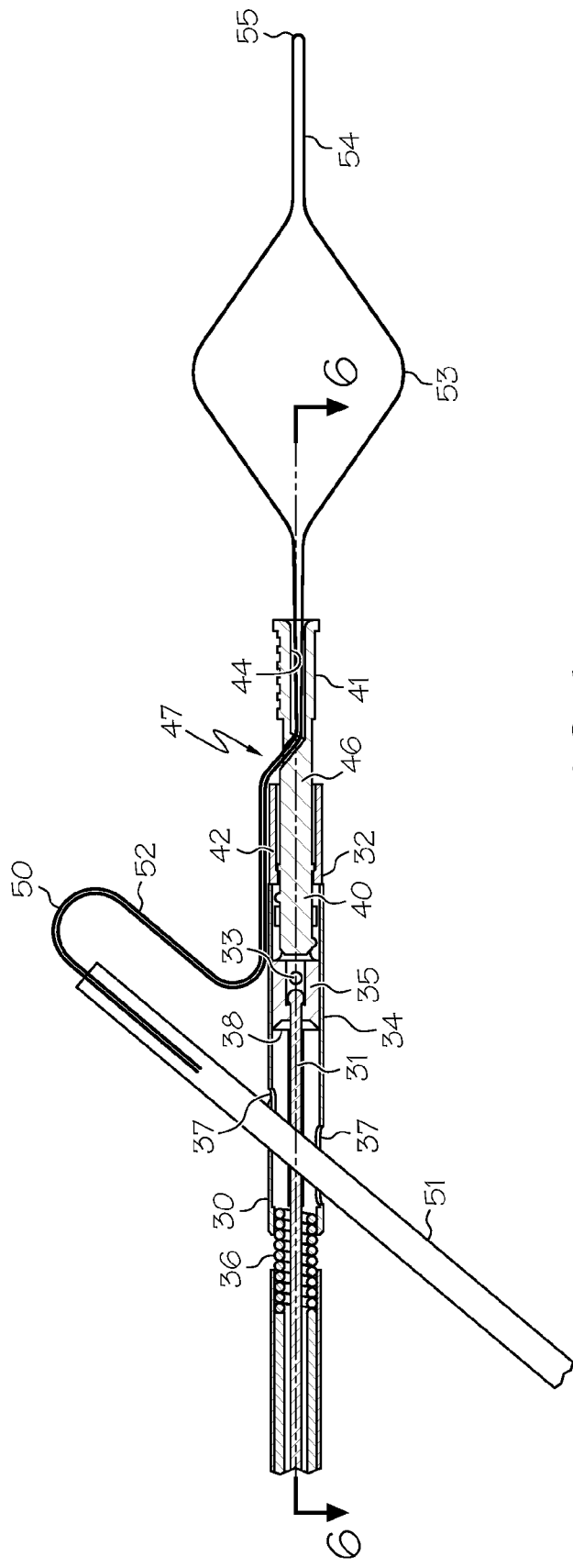
FIG. 5 depicts a cross-sectional side view of an applicator, knotting element, and threader.
Figure 6:
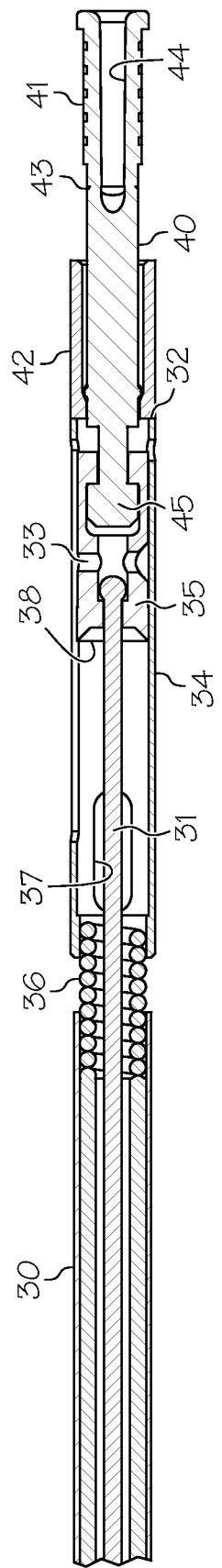
FIG. 6 depicts a cross-sectional top view of an applicator and knotting element.

FIGS. 5-6 illustrate an example of a knotting element (40) loaded onto an applicator (30). The applicator (30) includes a housing (34) connected to the flexible shaft (36) dimensioned to fit in the working channel of an endoscopic. A wire (31) is attached to an actuator (not shown) and a coupling (35). By pushing and pulling the wire (31) the coupling (35) slides axially relative the housing (35) between a distal position where the coupling (35) extends beyond the distal end (32) and a proximal position where the cutting edge (38) extends beyond the ports (37). The ports (37) on the housing (34) are circumferentially aligned with the coupling (35). The pin (33) on coupling (35) travels in a longitudinal slot in the housing (34) thus maintaining the relative angular orientation of the coupling (35) and housing (34).

The knotting element (40) is attached to the applicator (30) by interfacing the complimentary couplings (35, 45). Two motions may be used to attach the knotting element (40) to the applicator (30) in this embodiment. First, the couplings (35, 45) are engaged laterally moving the coupling (45) into the coupling (35) when in its distal position. The knotting element (40) may remain parallel to the applicator (30) during this first motion. Second, the engaged couplings (35, 45) are translated proximally such that they are pulled into the housing (34). The housing (34) prevents the couplings (35, 45) from moving laterally, thus securing the knotting element (40) onto the applicator (30). Naturally, the foregoing coupling arrangement is merely illustrative and one with ordinary skill in the art will recognize that a variety of other and other coupling arrangements may also be used.

Figure 3:
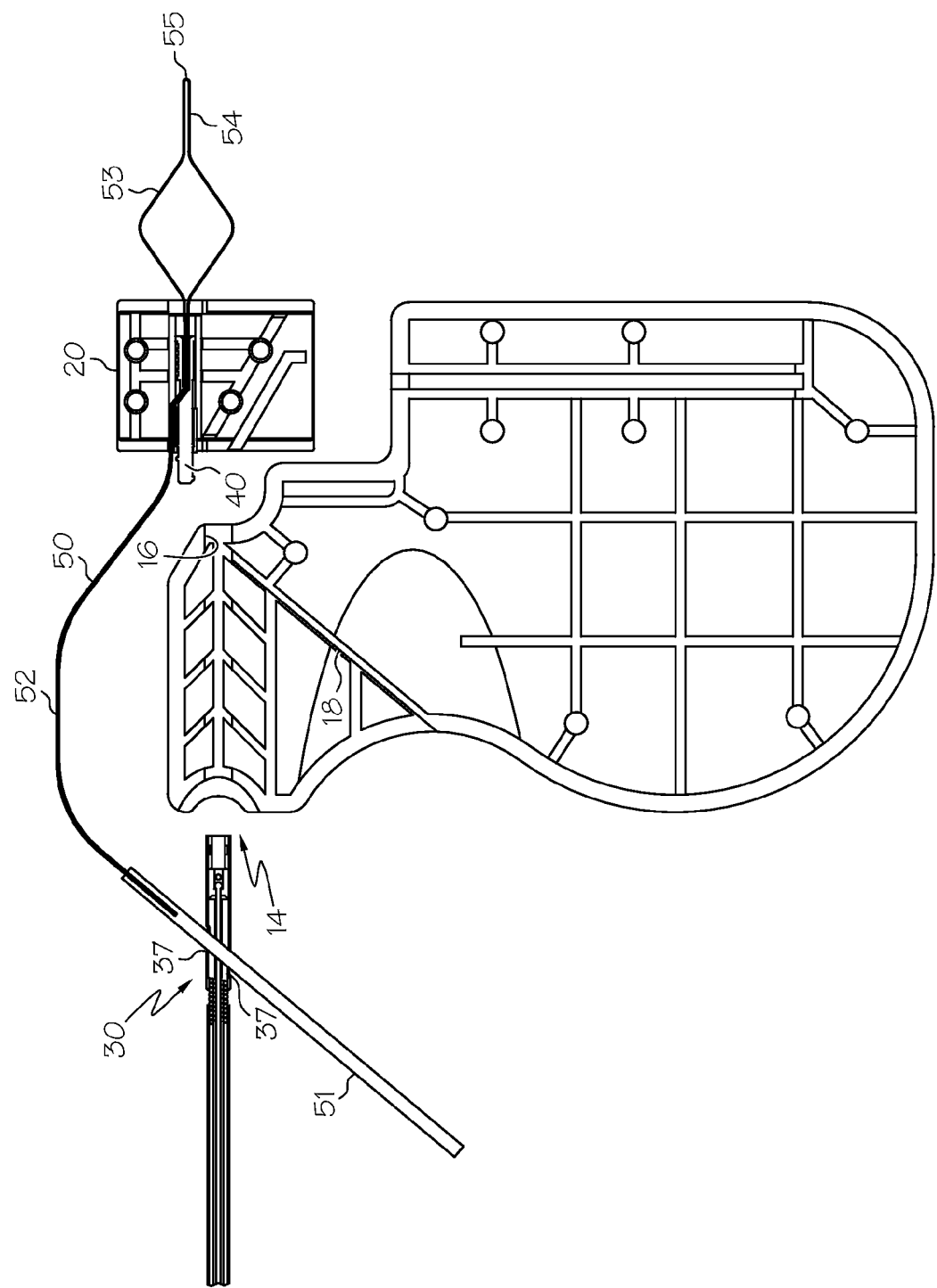
FIG. 3 depicts a side view of a knotting element loader with half the housing removed with the threader in an applicator.
Figure 4:
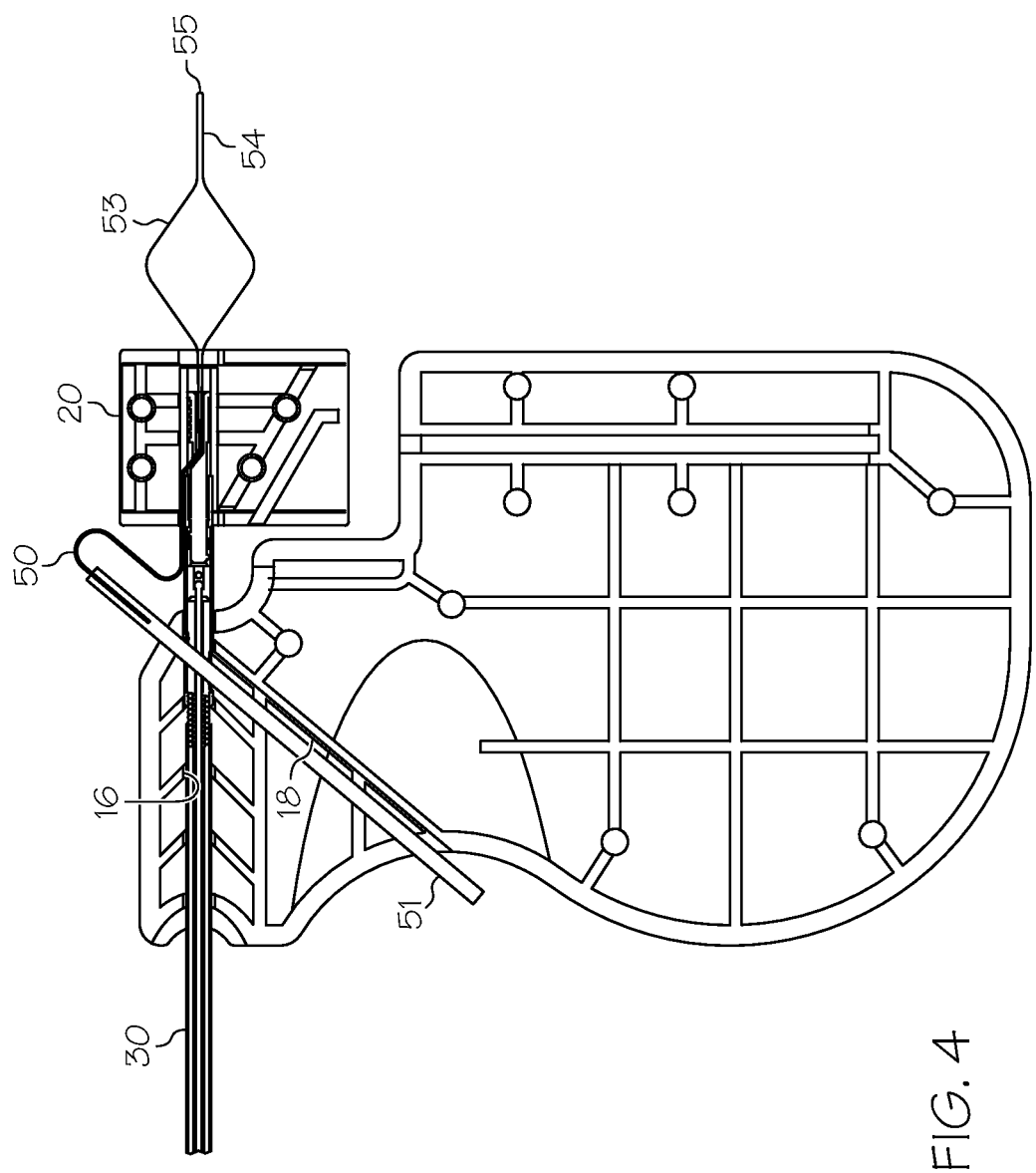
FIG. 4 depicts a side view of an anchor loader with half the housing removed with the applicator inserted in the loader.

FIGS. 2-4 demonstrate the operation of the loader (10). Initially, the applicator (30) to positioned next to the loader (10) as shown in FIG. 2. The knotting element (40) is held in the carriage (20) in a position parallel with the channel (16) but misaligned with the channel (16). Next, the rod (51) is passed through the ports (37). As shown in FIG. 4, the applicator (30) is introduced into port (14), preferably with the coupling (35) is pushed to its distal position. The rod (51) can slide longitudinally in the slot (18) but the slot (18) prevents rotation of the rod (51) thus facilitating proper angular alignment between the couplings (35, 45). The applicator (30) is advanced until it contacts the stop (22). In this embodiment the stop (22) is a slender blade dimensioned for insertion into the coupling (35). When the coupling (35) is fully engaged with the stop (22) angular and axial alignment is achieved between couplings (35, 45). The wall (11) on the housing (12) further facilitates alignment by providing a contrasting background to help users visualize the couplings (35, 45).

The carriage (20) moves relative the channel (16) in the same lateral motion as when the coupling (45) is designed to engage the coupling (45). Thus once the applicator (30) is fully inserted into the loader (10) and the couplings (35, 45) aligned, the carriage (20) can be depressed to engage the couplings (35, 45). The wire (31) may then be pulled so that the couplings (35, 45) translate into the housing (34). The applicator (30) may then be retracted from the channel (16). Since the knotting element (40) is now secured to the applicator (30), the knotting element (40) and threader (50) will similarly retract from the carriage (20), thus resulting in the assembly shown in FIG. 5.

The knotting element (40) of the present embodiment includes an inner tubular member (41), a stem (46) intermediate the coupling (45) and the inner tubular member (41), and an outer tubular member (42) that can slide axially relative the stem (46). When the knotting element (40) is secured to the applicator (30), the outer tubular member (42) engages the distal end (32) of the housing (34). A nonlinear suture path is defined by the longitudinal bore (44) of the inner tubular member (41) and the lateral port (47). One with ordinary skill in the art will recognize that the embodiment shown here is only one example of a suitable knotting element and that the teachings herein may be equally applied to other designs and types of knotting elements, including without limitation clips, spools, self-locking toothed elements, and the like.

The threader (50) is a flexible guide used for delivering suture in the intended path of the knotting element (40) and applicator (30). In this embodiment the threader (50) comprises proximal portion shown here as an elongate and relatively stiff rod (51). A wire connected to the rod (51) creates an medial portion (52) extending through the suture path. A distal portion extends distally from longitudinal bore (44) that includes a flared loop portion (53) and a narrow portion (54). As shown here the medial and distal portions are formed from a single loop of wire. Thus, the medial portion (52) is this embodiment comprises two adjacent and parallel wires. Naturally, other embodiments are also contemplated.

As shown in FIG. 5, the threader (50) is preloaded in the desired suture path for the knotting element (40) and applicator (30). In use, one or more strands of suture are passed through the flared loop portion (53). The rod (51) is then pulled proximally causing the wire to follow. Continued pulling of the threader (50) will pull the wire completely through the suture path and the ports (37). The suture threaded through the flared loop potion will migrate to the distal end (55) and will likewise be pulled through suture path and the ports (37). As a result, the suture will be successfully threaded in the knotting element (40) and applicator (30), with one end extending proximally from the port (37) and the other end extending distally from the longitudinal bore (44). The threader (50) may be as a stand-alone device or bundled with other devices, such as being preloaded in a knotting element, preloaded in a loader, or preloaded in an applicator.

The knotting element (40) is now ready for surgical deployment. The applicator (30) with engaged and threaded knotting element (40) is delivered to the surgical site, which in this embodiment would typically involve pushing the devices through a endoscope working channel. After desired tensioning of the suture by pulling the end extending proximally from the port (37), the wire (31) can be tensioned to translated the couplings (35, 45) proximally relative the housing (34). The stem (46) and inner tubular member (41) will also translate proximally; however, the outer tubular member (42) engages the distal end (32) causing the outer tubular member (42) to translate distally relative the stem (46). Continue tensioning of the wire (31) will force the outer tubular member (42) over the port (47) and inner tubular member (41) until the inner and outer tubular members (41, 42) are co-extensive with the suture crimped there between. Stress concentration detents (43) result in a frangible connection between the inner tubular member (41) and the stem (46), so further tensioning of the wire (31) will cause the co-extensive inner and outer tubular members (41, 42) to separate from the stem (46). Still further tensioning of the wire (31) will translate the cutting surface (38) to engage the suture passing through the ports (37) thus shearing the suture. The applicator (30), coupling (45), and stem (46) can then be withdrawn from the surgical site, leaving the suture securely fastened between the inner and outer tubular sections (41, 42).

Preferably the one or more of the foregoing devices will be processed before surgery. First, a new or used devices are obtained and if necessary cleaned. The devices can then be sterilized. In one sterilization technique, the devices are placed in a closed and sealed container, such as a plastic or TYVEK bag. Optionally, an applicator (30) and one or more loaders (10), each with preloaded knotting elements (40) and threaders (50), could be bundled as a kit and sealed in the same container. The container is then placed in a field of radiation that can penetrate the container, such as gamma radiation, x-rays, or high-energy electrons. The radiation kills bacteria on the devices and in the container. The sterilized devices can then be stored in the sterile container. The sealed container keeps the devices sterile until it is opened in the medical facility.

Having shown and described various embodiments and examples, further adaptations of the methods and apparatuses described herein can be accomplished by appropriate modifications by one of ordinary skill in the art without departing from the scope of the present invention. Several of such potential modifications have been mentioned, and others will be apparent to those skilled in the art. Accordingly, the scope of the present invention should be considered in terms of the following claims and is understood not to be limited to the details of structure, materials, or acts shown and described in the specification and figures.

The invention claimed is:
1. A surgical system comprising:
a) an applicator tool comprising a proximal end with an actuator, a distal end comprising a coupling operatively connected to the actuator, and an elongate shaft extending between the proximal and distal ends;
b) a surgical knotting element comprising a coupling complementary to the coupling of an applicator tool, the surgical knotting element further comprising a suture path, the surgical knotting element comprising a fastened configuration whereby suture positioned in the suture path is cinched and an unfastened configuration;

c) a loader separate from the applicator tool, the loader comprising
  (i) a housing comprising a channel dimensioned to receive the distal end of the applicator tool;
  (ii) a carriage receiving the surgical knotting element, the carriage being moveable in a transverse direction relative the channel between a first position where the knotting element is misaligned with the channel and a second position where, when the applicator tool is received by channel, the couplings are engaged with one another; and
  (iii) an elongate flexible suture guide positioned in the suture path, the suture guide comprising a flared loop portion.

2. The device of claim 1, wherein the flexible suture guide further comprises a stiff elongate rod.

3. The device of claim 2, wherein the stiff elongate rod is dimensioned to be transversely received by the applicator tool and the housing further comprises a slot transverse the channel dimensioned to receive the stiff elongate rod.

4. The device of claim 1, further comprising a resilient tube on carriage receiving the knotting element.

5. The device of claim 1, wherein the flared loop portion is formed from a wire.

6. The device of claim 5, wherein the threader further comprises a proximal portion and a medial portion, the medial portion being formed from the same loop of wire.

7. The device of claim 6, wherein the proximal portion is a stiff elongate rod and the threader comprises a loop of wire attached to the stiff elongate rod forming the medial portion and flared loop portion.

8. A method of processing a device for surgery, comprising:
  a) obtaining the device of claim 1;
  b) sterilizing the device; and
  c) storing the device in a sterile container.

* * * * *